United States Patent [19]

Cogley, Jr.

[11] 4,116,072

[45] Sep. 26, 1978

[54] METHOD AND APPARATUS FOR DETERMINING THE DENSITY OF DRY FIBERS

[75] Inventor: Robert W. Cogley, Jr., Lancaster, Pa.

[73] Assignee: Armstrong Cork Company, Lancaster, Pa.

[21] Appl. No.: 822,052

[22] Filed: Aug. 5, 1977

[51] Int. Cl.² .............................................. G01N 9/02
[52] U.S. Cl. ...................................................... 73/433
[58] Field of Search ................................. 73/32 R, 433

[56] References Cited

U.S. PATENT DOCUMENTS

| 923,560 | 6/1909 | Mount | 73/32 |
|---|---|---|---|
| 2,373,026 | 4/1945 | Guyer et al. | 73/32 X |
| 2,720,109 | 10/1955 | Stirn et al. | 73/32 R |

Primary Examiner—Richard C. Queisser
Assistant Examiner—John P. Beauchamp

[57] ABSTRACT

A method and apparatus for determining the density of dry fibers, mainly in the form of fiber bundles. A sample of these dry fibers is weighed. The fiber bundles of these dry fibers are fed into the suction side of an air aspirator and opened into a combination of smaller fiber bundles and individual fibers as they exit from the pressure side of the aspirator. The combination of smaller fiber bundles and individual fibers passes through a chamber and is deposited onto a screen in the bottom of an enclosure. The enclosure is supported so that there is an open space under the screen, thereby allowing the air which is transporting the combination when the combination is deposited on the screen to pass through the screen and exit from the apparatus. The volume of the combination of smaller fiber bundles and individual fibers deposited on the screen in the enclosure is measured, and the density of the dry fibers is calculated using the measured weight and volume of the sample.

8 Claims, 3 Drawing Figures

U.S. Patent  Sept. 26, 1978  4,116,072
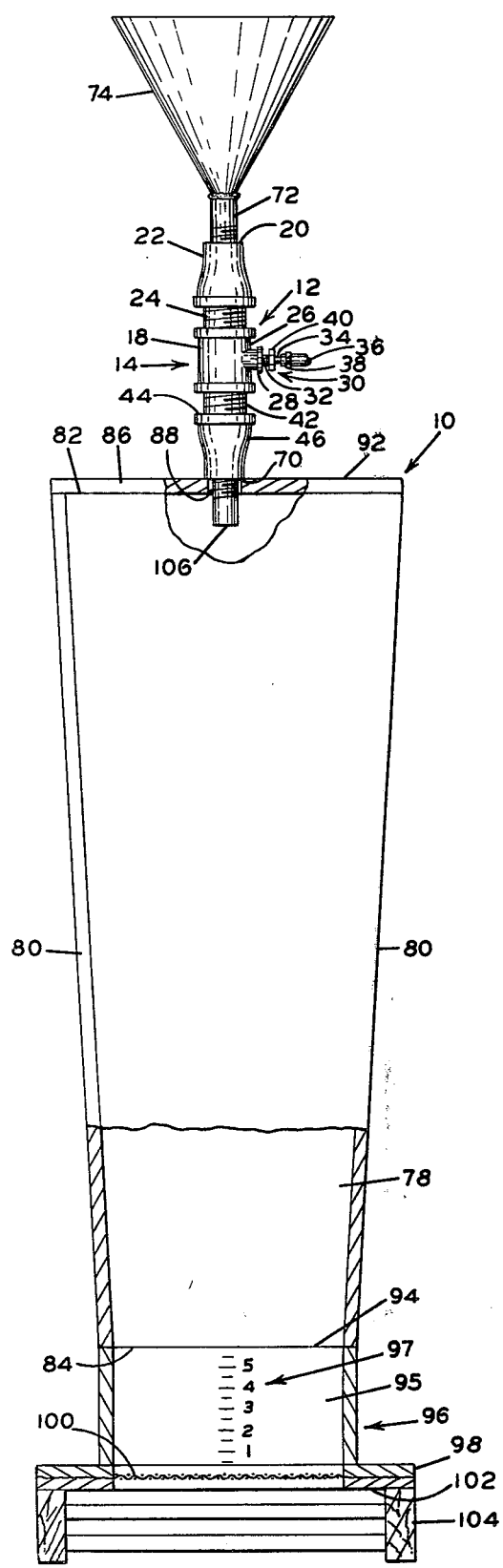
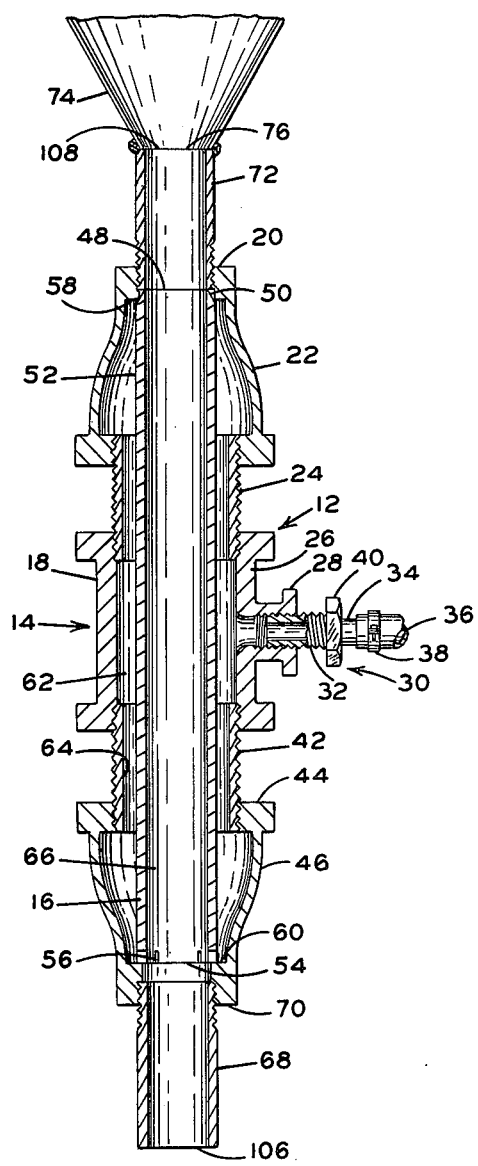
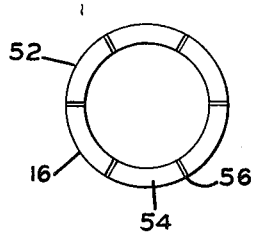

METHOD AND APPARATUS FOR DETERMINING THE DENSITY OF DRY FIBERS

BACKGROUND OF THE INVENTION

1. Field of the Invention

This invention relates to a method and apparatus for determining the density of fibrous material, and more particularly, to the method and apparatus for determining the density of dry fibers in the form of fiber bundles and individual fibers used in the manufacture of fibrous boards, panels, and tiles.

2. Description of the Prior Art

U.S. Pat. Nos. 3,209,587 and 3,060,724 appear to typify the state of the prior art. These patents are concerned with determining the volume and/or density of the actual fibers without including any of the voids around the fibers as part of the density. The claimed invention herein is directed to determining the density of dry fibers in a mass which includes the air voids in the mass in this density determination. Both of these prior art patents use measured gas pressure in determining the density of the material. The claimed invention does not use a measured gas pressure in its density determination.

SUMMARY OF THE INVENTION

A sample of dry fibers, mainly in the form of fiber bundles, is weighed. The dry fibers of this sample are then fed into the in-feed end, the suction end, of an air aspirator. The fibers of the sample are drawn into and pass through the aspirator and are opened into a combination of smaller fiber bundles and individual fibers as they pass through the out-feed end, the pressure end, of the aspirator. The out-feed end of the aspirator fits into an opening in the top of a chamber. The dry fibers exiting the out-feed end of the air aspirator enter the chamber and the combination of smaller fiber bundles and individual fibers pass through the chamber and are deposited on a screen attached to the bottom of a box, the screen allowing the air in which the combination of smaller fiber bundles and individual fibers is moving to pass therethrough, thereby separating the combination from the excess air. The box having the attached screen at the bottom is supported by any conventional support so long as there is at least a passage for the air passing through the screen to exit to the atmosphere.

The volume of the deposited combination is then measured. The deposited combination at this point is essentially a mat of the combination of smaller fiber bundles, individual fibers, and the air voids between them, the mat having measurable length, width, and thickness dimensions. Using the measured weight of the sample and the volume of the sample in its deposited combination form just described, the density of the dry fibers in this mat form can now be calculated.

It is an object of the present invention to provide a simple and accurate method for determining the density of a mat of dry fibers, including the voids between the fibers as part of the volume of the fibers.

A further object of the present invention is to provide an apparatus for determining the density of a sample of dry fibers of known weight when the dry fibers are laid up in the form of a mat.

Another object of the invention is to provide an apparatus for determining the density of a sample of dry fibers of known weight whose use may be mastered quickly and accurately by an unskilled operator.

Yet another object of the invention is to provide a method and apparatus for determining the density of a dry fibrous mat which simulates the product which will be made from the dry fibers.

BRIEF DESCRIPTION OF THE DRAWINGS

FIG. 1 is a partial sectional view in elevation of the complete assembled apparatus;

FIG. 2 is a cross-sectional view in elevation of the air aspirator of the apparatus; and FIG. 3 is a bottom view of the lower end of the tube of the air aspirator of the apparatus.

DESCRIPTION OF THE PREFERRED EMBODIMENT

Dry fibers, e.g., mineral wool, fiberglass, cellulose, for use in the manufacture of boards, panels, or tiles for ceilings and/or walls are normally received at the manufacturing facility in a large bale. However, these same fibers may also be received at the manufacturing facility in an unbaled condition. In both situations, the fibers are in the form of large fiber bundles. To use these fibers in the manufacture of boards, panels, and tiles, it is necessary to open up the fibers into smaller fiber bundles and individual fibers. Since the dry fibers can vary in density and since the density of a fibrous mat made up of dry laid fibers which have been opened up into bundles smaller than the original fiber bundles and into individual fibers is directly related to the strength of the board, panel, or tile manufacture from these fibers, it is important to determine this density so that various manufacturing parameters can be adjusted accordingly. The apparatus 10 shown in FIG. 1 and a conventional measuring device such as a ruler can be used to determine this density figure for the dry fibers.

A sample of dry fibers in the form of large fiber bundles is removed for a conventional supply of mineral wool fibers. The sample of fibers is then weighed. This weighed sample of dry fibers is then fed into air aspirator 12.

Air aspirator 12 has a body portion 14 comprising a tube 16 and a sleeve 18. The sleeve has a nominal inside diameter of 2 inches and is constructed by screwing together conventional pipe adapters, nipples, and fittings. The upper end 20 of sleeve 18 is the 1¼ inches end of a 1¼ inch IPS–2 inch IPS adapter 22. Adapter 22 is screwed onto 2 inch IPS nipple 24. Nipple 24 is screwed into 2 inch IPS tee fitting 26. The leg portion 28 of tee fitting 26 is adapted to receive a conventional ½ inch air line nipple 30 having screw threads 32 on the end of the nipple 30 which screws into leg portion 28 of the tee fitting, a tube 34 at the other end of the nipple over which a conventional ½ inch air supply line hose 36 is positioned and held thereon by a conventional clamp 38, and a hexagonal nut 40 for screwing the nipple into the leg portion 28 of tee fitting 26. The tee fitting 26 is screwed onto a 2 inch IPS nipple 42. Nipple 42 is screwed into the 2 inch end 44 of the 2 inch IPS - 1¼ inch IPS adapter 46.

The tube 16 is a 1¼ inch IPS pipe, 10½ inches long. The upper end 48 of tube 16 has a ¼ inch bevel 50. The lower end 54 of tube 16 has six slots 56 cut therein. Slots 56 are 1/16 inch wide and 3/16 inch deep, have a length equal to the thickness of the wall of tube 16, and are equidistantly spaced around the circumference of end 54 of tube 16.

Sleeve 18 can be disassembled at any of the joints between the adapters 22 and 46, nipples 24 and 42, and tee fitting 26. Tube 16 is then inserted into sleeve 18 with the end 48 of tube 16 adjacent end 20 of adapter 22. The bevel 50 of end 48 of tube 16 abuts shoulder 58 of adapter 22 and end 54 of tube 16 abuts shoulder 60 of adapter 46 when the tube 16 is inserted in sleeve 18 and sleeve 18 is reassembled at the same point where it was disassembled to insert tube 16.

When the tube 16 is positioned in sleeve 18 so that bevel 50 abuts shoulder 58 and end 54 abuts shoulder 60, there is an enclosed space 62 formed between the outer surface 52 of tube 16 and the inner surface 64 of sleeve 18 and between the shoulders 58 and 60 of adapters 22 and 46 respectively. The space 62 has a shape roughly similar to that of a sleeve having a wall approximately ½ inch thick and tapered at either end. Air at a pressure of about 60 psi is fed into this space 62 through conventional air hose 36, nipple 30, and leg portion 28 of tee fitting 26. This infeed air pressure may be as low as 20 psi when the air is supplied through a conventional air line having at least a ½ inch inside diameter. The air entering space 62 exits therefrom through slots 56 in the bottom end 54 of tube 16 into the interior 66 of tube 16 in a downward direction. The air exiting body portion 14 of aspirator 12 through slots 56 of tube 16 causes a vacuum or suction action at the upper end 20 of adapter 22, which is also the upper end of body portion 14 of aspirator 12. The aspirator 12 would function properly with just the main body portion 14 above described. However, for convenience, a 1¼ inch IPS nipple 68 is screwed into end 70 of adapter 46. The length of nipple 68 can be about 3 inch, but this length is not critical. A 1¼ inch IPS nipple 72 is screwed into end 20 of adapter 22. The length of nipple 72 can be about 3 inch, but this length is also not critical. A funnel 74 of any convenient size, e.g., 12 inches in diameter and 12 inches in height, is fashioned from sheet metal and welded to the upper end 76 of nipple 72. This funnel is convenient but not critical.

A chamber 78 is made of any convenient construction material which has sufficient structural strength to carry the weight of air aspirator 12. An example of such construction material is ¾ inch plywood. The chamber is formed by fastening together in any conventional manner, e.g., with nails or screws, four identical boards 80 which are the sides of chamber 78. The cross section of the chamber 78 is that of a square. The upper end 82 of the chamber measures approximately 15 inches. The lower end 84 of the chamber measures approximately 12 inches. The height of the chamber is approximately 4 feet.

A lid 86 can be fixedly or removably fastened over the upper end 82 of chamber 78. As shown in FIG. 1, the lid 86 is fastened to the upper end of the four sides 80 in any conventional manner, e.g., with nails or screws. Lid 86 has a hole 88 located at its center. The diameter of hole 88 is larger than the outside diameter of nipple 68 of aspirator 12, but smaller than the outside diameter of adapter 46 at end 70. The end 70 of adapter 46 rests on the top 92 of lid 86 around hole 88.

The lower end 84 of chamber 78 is removably positioned over the opening of the upper end 94 of separating box 96. The separating box 96 has a 12 × 12 inch square opening throughout its 6¾ inch height. Therefore, the opening of the upper end 94 of separating box 96 mates with the opening of the lower end 84 of chamber 78. The base 98 of separating box 96 has outside dimensions of 18 × 18 × 1½ inches. This base 98 has a square opening 12 × 12 inches cut through its entire thickness at its center. A filtering device 100, e.g., a conventional window screen, is located at the midpoint of the thickness of base 98. The screen 100 should cover at least the 12 × 12 inch square opening in the base 98 and extend beyond the opening whatever distance is required to fasten the screen to the base. This base 98 can be conveniently constructed by positioning a piece of screen between two ¾ inch pieces of plywood cut to the dimensions for base 98.

The bottom 102 of base 98 is positioned on any convenient support 104. The only requirements for support 104 are that it has the structural strength to carry the combined weight of aspirator 12, the materials forming the chamber 78, and separating box 96, that the 12 × 12 inch square opening of the box 96 not be obstructed, and that there be at least some passageway from the opening at the bottom 102 of box 96 to the atmosphere. On the inside of at least one of the sides 95 of separating box 96, a measuring device 97 is positioned. This measuring device 97 divides the 6 inch height of the box 96 from the screen 100 to the upper end 94 of box 96 into inches and any convenient increments of inches.

In operation, the air pressure is turned on so that air enters the space 62 of aspirator 12 through the leg portion 28, nipple 30, and air supply line hose 36. The air exits space 62 through the six slots 56, travels downward through nipple 68, and goes out the out-feed end 106 of aspirator 12 into chamber 78. This air flow causes a vacuum or suction action at the in-feed end 108 of aspirator 12. The air continues through chamber 78, into separating box 96, through screen 100, and exits the box 96 into the atmosphere.

A weighed sample of mineral wood is manually broken into clumps of fiber bundles, which clumps should be about the same size as the in-feed end 108 of the aspirator. These clumps are put in the funnel and sucked into the in-feed end 108 by the suction action at this end of the aspirator. This suction action of the aspirator begins to break up the fiber clumps. The partially broken clumps pass through the interior 66 of tube 16 of the aspirator to the lower end 54 of tube 16. At the lower end 54 of tube 16, the partially broken clumps of mineral wool fiber bundles are subjected to the air stream entering the interior 66 of aspirator 12 through slots 56. This air stream and the decompression of negative pressure in the fiber bundles opens the fiber bundles in the partially broken clumps of mineral wool into smaller fiber bundles and individual fibers. This same air stream blows this combination of smaller fiber bundles and individual fibers out the out-feed end 106 of the aspirator and into the upper end of chamber 78. At this point, the air pressure exerted on the combination of smaller fiber bundles and individual fibers is reduced because of the larger dimensions of the chamber. The combination of smaller fiber bundles and individual fibers are carried from the out-feed end 106 of the aspirator through the remaining length of the chamber by this air. The air continues to transport the fibers into the separating box 96 where the fibers are deposited on screen 100. The air continues through the screen and exits to the atmosphere.

After the sample of known weight of mineral fibers has been fed through the aspirator, the chamber, and deposited on the screen of the separating box, the aspirator 12, and the materials forming the chamber 78 are removed from the separating box 96. The dry fibers deposited on the screen in the box are manually leveled and the height of the fibrous mat is determined. Using this measured height value of the fibrous mat and the known 12 × 12 inch dimensions of the box, the volume of the dry laid fibrous mat can be ascertained.

Using the measured values of the weight of the dry fiber sample and the volume of the dry laid mat of dry fibers, the density of this fibrous mat of dry fibers can be calculated.

From a material economics point of view, it is normally desirable to manufacture a fibrous board, panel, or tile at the lowest density possible. Using the apparatus and method of this invention enables one to determine what the lowest density should be for a particular product using a particular process. Besides determining what is the lowest density that is usable for a particular product and a particular process, the determination of the density for specific fibers being used in the process will allow the process parameters to be varied to produce the product most economically. This would apply whether the manufactured fibrous product would use a dry-type process for making the fibrous board or a wet-type process. However, this particular method and apparatus is particularly well suited for fibrous products which are manufactured by a dry-type process.

In determining the density of the dry fibers which have been deposited on the screen 100 of the separating box and manually leveled to form a mat of uniform thickness, it may be desirable to compress these fibers before measuring the thickness of the mat. This can be accomplished by using a plate slightly less than 12 × 12 inch square on top of the mat of fibers whose density is to be determined and adding whatever weight is desired. The reason for compressing the fibers before measuring the thickness of the mat of deposited fibers is to have the fibrous mat whose density is being determined more closely approximate the state of the fibers as they are used in the fibrous product being manufactured.

Stated another way, the condition and state of the fibers being tested to determine their density should duplicate as closely as possible the state and condition of the fibers as they are being used in the fibrous product being manufactured. By way of example only, the state and condition of dry mineral wool fibers deposited in a mat on the screen most closely duplicated the state and condition of these fibers used in a dry-type process for manufacturing fiberboard products, such as the process set forth in U.S. patent application Ser. No. 780,419, when 261 grams were placed over the manually leveled mat of dry fibers. Accordingly, the density of the mat of dry mineral wool fibers was calculated using the volume measured while the fibers were in this compressed condition. The added weight tested for this particular product and process when determined the density of the mat of dry mineral wool fibers deposited on the screen was in the range of from no weight to 4,261 grams, including these weights. The amount of weight which need be added, if in fact any need be added, for each particular product and process must be determined by experimenting with various added weights until the most appropriate one is found. It is also possible that the air pressure fed into the space 62 of the air aspirator 12 may be adjusted to vary the extent to which the original fiber bundles are opened into smaller fiber bundles and individual fibers to more closely approximate how the fibers being used in the manufactured product are opened up.

What is claimed is:

1. A method for determining the density of dry fibers mainly in the form of fiber bundles comprising the steps of:
   (a) weighing a sample of said dry fibers,
   (b) opening the fiber bundles of the sample to disperse said fiber bundles into a combination of smaller fiber bundles and individual fibers by the use of pressurized air,
   (c) depositing the combination of smaller fiber bundles and individual fibers onto a screen,
   (d) measuring the volume of said deposited combination, and
   (e) calculating the density of the dry fibers using the measured weight and volume of the sample.

2. The method of claim 1 wherein the pressurized air is passed through an air aspirator, said pressurized air being supplied to said air aspirator at a pressure of at least 20 psi through a supply line having at least a ½ inch inside diameter.

3. An apparatus for use in determining the density of a sample of dry fibers of known weight, said dry fibers being mainly in the form of fiber bundles, comprising:
   (a) a means for opening the fiber bundles into a combination of smaller fiber bundles and individual fibers, said opening means having an in-feed end and an out-feed end,
   (b) a means for supporting said opening means,
   (c) a separating means having one end being open and the opposite end being covered with a filtering means to separate the combination of smaller fiber bundles and individual fibers from the medium in which said combination is moving so that a volume of said combination is retained on said filtering means,
   (d) a chamber formed by an enclosure having one end adapted to receive the out-feed end of said opening means and the opposite end adapted to communicate with the open end of said separating means and positioned on the open end of said separating means,
   (e) the out-feed end of said opening means projecting into said chamber, and
   (f) a means for supporting the separating means with the filtering means end of said separating means being adjacent said supporting means.

4. The apparatus of claim 3 additionally comprising a means for measuring the thickness of the volume of said combination retained on the filtering means in said separating means.

5. The apparatus of claim 3 wherein said opening means comprises a pressurized air device.

6. The apparatus of claim 5 wherein the pressurized air device comprises an air aspirator.

7. The apparatus of claim 3 wherein said filtering means comprises a screen.

8. The apparatus of claim 3 wherein said means for supporting said opening means comprises said enclosure end adapted to receive the out-feed end of said opening means.

* * * * *